US011969242B2

(12) United States Patent
Lotan et al.

(10) Patent No.: US 11,969,242 B2
(45) Date of Patent: *Apr. 30, 2024

(54) ORTHODONTIC SYSTEM WITH TOOTH MOVEMENT AND POSITION MEASURING, MONITORING, AND CONTROL

(71) Applicant: Dror Ortho Design LTD (Aerodentis), Jerusalem (IL)

(72) Inventors: Tal Lotan, Jerusalem (IL); Shachar Ronen, Jerusalem (IL)

(73) Assignee: Dror Ortho Design Ltd. (Aerodentis), Jerusalem (IL)

( * ) Notice: Subject to any disclaimer, the term of this patent is extended or adjusted under 35 U.S.C. 154(b) by 359 days.

This patent is subject to a terminal disclaimer.

(21) Appl. No.: 17/021,914

(22) Filed: Sep. 15, 2020

(65) Prior Publication Data

US 2020/0405191 A1    Dec. 31, 2020

Related U.S. Application Data

(62) Division of application No. 15/059,140, filed on Mar. 2, 2016, now Pat. No. 10,806,376.

(51) Int. Cl.
*A61B 5/11* (2006.01)
*A61B 5/00* (2006.01)
(Continued)

(52) U.S. Cl.
CPC ........... *A61B 5/1111* (2013.01); *A61B 5/0002* (2013.01); *A61B 5/0088* (2013.01);
(Continued)

(58) Field of Classification Search
CPC ......... A61C 7/002; A61C 7/08; A61C 1/0015; A61C 1/052; A61C 19/04; A61B 1/04; A61B 1/24

See application file for complete search history.

(56) References Cited

U.S. PATENT DOCUMENTS 3,975,825 A    8/1976 Smith
4,823,488 A    4/1989 Fottner
(Continued)

FOREIGN PATENT DOCUMENTS

EP    3060159 A1    8/2016
JP    2008-532563 A    8/2008
(Continued)

OTHER PUBLICATIONS

Communication dated Nov. 30, 2020 in related European Patent Application No. 17783584.0.
(Continued)

*Primary Examiner* — Nicholas D Lucchesi
(74) *Attorney, Agent, or Firm* — Rivka Friedman

(57) ABSTRACT

An orthodontic system and method for moving and aligning at least one tooth of a set of teeth of at least one of an upper jaw and a lower jaw of a patient. In the system and method an orthodontic appliance can be provided which may include a force exerting member for applying a force to and moving the at least one tooth, a tooth movement sensor member for obtaining at least one of tooth movement data, tooth position data, and tooth identification data, and a tooth movement monitor for calculating at least one of an amount of tooth movement and tooth position from the at least one of the tooth movement data, the tooth position data, and the tooth identification data obtained with the tooth movement sensor arrangement. An electronic control console may be operatively connected to the force exerting member and in data communication with the tooth movement monitor, for controlling the operation of the force exerting member based on the at least one of the tooth movement data, the tooth position data, and the tooth identification data received from the tooth movement monitor.

21 Claims, 4 Drawing Sheets

(51) Int. Cl.

| | | |
|---|---|---|
| *A61B 5/107* | (2006.01) | |
| *A61C 1/00* | (2006.01) | |
| *A61C 1/05* | (2006.01) | |
| *A61C 7/08* | (2006.01) | |
| *A61C 19/04* | (2006.01) | |
| *A61B 90/00* | (2016.01) | |

(52) U.S. Cl.
CPC .......... *A61B 5/1076* (2013.01); *A61B 5/1128* (2013.01); *A61B 5/682* (2013.01); *A61C 1/0015* (2013.01); *A61C 1/052* (2013.01); *A61C 7/08* (2013.01); *A61C 19/04* (2013.01); *A61B 2090/064* (2016.02)

(56) References Cited

U.S. PATENT DOCUMENTS

| | | | |
|---|---|---|---|
| 4,823,788 | A | 4/1989 | Smith et al. |
| 7,819,661 | B2 | 10/2010 | Nadav |
| 10,806,376 | B2 | 10/2020 | Lotan et al. |
| 10,820,965 | B2 | 11/2020 | Lotan et al. |
| 2002/0094509 | A1 | 7/2002 | Durbin et al. |
| 2007/0065768 | A1 | 3/2007 | Nadav |
| 2009/0017422 | A1* | 1/2009 | Creamer .............. A61C 19/066 433/215 |
| 2009/0220921 | A1* | 9/2009 | Abolfathi ................. A61C 7/08 433/229 |
| 2012/0148976 | A1 | 6/2012 | Brawn |
| 2013/0040264 | A1* | 2/2013 | Scurtescu ................ A61C 7/00 433/119 |
| 2015/0114439 | A1 | 4/2015 | Henderson et al. |
| 2015/0173856 | A1 | 6/2015 | Lowe et al. |
| 2015/0230885 | A1 | 8/2015 | Wucher |
| 2016/0228212 | A1 | 8/2016 | Salah et al. |
| 2017/0251954 | A1 | 9/2017 | Lotan et al. |
| 2018/0078334 | A1 | 3/2018 | Lotan et al. |
| 2021/0145544 | A1 | 5/2021 | Lotan et al. |

FOREIGN PATENT DOCUMENTS

| | | | |
|---|---|---|---|
| JP | 2014-131774 | A | 7/2014 |
| WO | 2007/137302 | A2 | 11/2007 |
| WO | 2015/040577 | A1 | 3/2015 |
| WO | 2015/058284 | A1 | 4/2015 |
| WO | 2017/149497 | A3 | 10/2017 |
| WO | 2018/051303 | A2 | 3/2018 |

OTHER PUBLICATIONS

Office Action (and English Translation) issued in counterpart Japanese patent application No. 2019-515331 dated Nov. 30, 2020.
Office Action issued in counterpart Japanese patent application No. 2018-565468, dated Nov. 2, 2020, 4 pp.
Advisory Action (PTOL-303) received for U.S. Appl. No. 15/269,465, dated Jul. 26, 2018, 03 pages.
Advisory Action received for U.S. Appl. No. 15/059,140, dated Nov. 29, 2019, 3 pages.
Applicant Initiated Interview Summary (PTOL-413) received for U.S. Appl. No. 15/269,465, dated May 14, 2019, 3 pages.
Authorized Officer: Bruckner, Benedikt, "Partial Search Report" dated Jul. 5, 2017 issued in corresponding PCT Application No. PCT/IB2017/051233.
Authorized Officer: Bruckner, Benedikt, Invitation to Pay Additional Fees in counterpart PCT application No. PCT/IB2017/051233, dated Apr. 5, 2017, 17 pp.
Ex Parte Quayle Action received for U.S. Appl. No. 15/059,140, dated Dec. 30, 2019, 4 pages.
"Final Office Action", U.S. Appl. No. 15/269,465, dated Mar. 19, 2018, 18 pp.
"Non-Final Office Action", U.S. Appl. No. 15/269,465, dated Jul. 28, 2017, 20 pp.
Examiner initiated interview summary received for U.S. Appl. No. 15/269,465, dated Mar. 20, 2020, 1 page.
"Non-Final Office Action", U.S. Appl. No. 15/059,140, dated Nov. 30, 2017, 6 pp.
Advisory Action issued in related U.S. Appl. No. 15/269,465, dated Jul. 26, 2018, 8 pp.
Final Office Action issued in related U.S. Appl. No. 15/269,465, dated Aug. 22, 2019, 20 pp.
Non-Final Office Action issued in related U.S. Appl. No. 15/269,465, dated Jan. 11, 2019, 20 pp.
Notice of Allowance issued in counterpart U.S. Appl. No. 15/269,465, dated Mar. 20, 2020, 14 pp.
Final Rejection received for U.S. Appl. No. 15/059,140, dated Aug. 8, 2019, 8 pages.
Final Rejection received for U.S. Appl. No. 15/269,465, dated Aug. 22, 2019, 19 pages.
Non-Final Rejection received for U.S. Appl. No. 15/059,140, dated Jan. 14, 2019, 7 pages.
Non-Final Rejection received for U.S. Appl. No. 15/269,465, dated Jan. 11, 2019, 17 pages.
Notice of Allowance and Fees Due (PTOL-85) dated Aug. 24, 2020 for U.S. Appl. No. 15/059,140.
Notice of Allowance and Fees Due (PTOL-85) dated Jun. 29, 2020 for U.S. Appl. No. 15/269,465.
Notice of Allowance and Fees Due (PTOL-85) dated May 14, 2020 for U.S. Appl. No. 15/059,140.
Notice of Allowance and Fees Due (PTOL-85) dated Sep. 22, 2020 for U.S. Appl. No. 15/059,140.
Notice of Allowance received for U.S. Appl. No. 15/059,140, dated Jan. 27, 2020, 6 pages.
Notice of Allowance received for U.S. Appl. No. 15/269,465, dated Mar. 20, 2020, 13 pages.
Office Action issued in counterpart Korean patent application No. 10-2018-7028372, dated Mar. 2, 2020, 6 pp.
Office Action dated Jun. 1, 2020 in JP Patent Application No. 2018-565468.
Officer Benedikt Bruckner, "Invitation to Pay Additional Fees and, Where Applicable, Protest Fee", International Patent Application PCT/IB2017/051233, dated Jul. 5, 2017, 17 pp.
Officer Patricia Sanchez Gomez, "Invitation to Pay Additional Fees and, Where Applicable, Protest Fee", International Patent Application PCT/IB2017/055635, dated Dec. 20, 2017, 13 pp.
Officer: Bruce Fortune, "International Search Report and the Written Opinion", International Patent Application PCT/IB2017/051233, Completed Jun. 29, 2017, 23 pp.
Officer: Bruce Fortune, "International Search Report and the Written Opinion", International Patent Application PCT/IB2017/055635, Completed Dec. 5, 2017, 20 pp.
Office Action issued in counterpart European patent application No. 17716012.4, dated Oct. 13, 2019, 5 pp.
Controller of Patents: Aiswarya P N, Examination Report issued in Indian patent application No. 201927014905, dated Apr. 30, 2021, 5 pp.
Examination Report issued in counterpart Australian patent application No. 2017225621, dated Mar. 12, 2021, 6 pp.
Examination Report issued in counterpart Australian patent application No. 2017225621, dated Sep. 16, 2021, 3 pp.
Office Action issued in counterpart Israeli patent application No. 261491, dated Aug. 29, 2021, 6 pp.
Office Action issued in counterpart Korean patent application No. 10-2018-7028372, dated Mar. 2, 2020, 6 pp. w/ translation.
Office Action issued in Israeli patent application No. 261491, dated Dec. 7, 2021, 4 pp.
Patent Controller: Ritesh Kumar, Examination Report issued in counterpart Indian patent application No. 201827037049, dated May 21, 2021, 11 pp.
Requirement for Restriction/Election dated Oct. 26, 2022 for U.S. Appl. No. 17/087,345.
Shuiwei Xie, Examination Report issued in Australian patent application No. 2017328249, dated May 21, 2021, 3 pp.

\* cited by examiner

ORTHODONTIC SYSTEM WITH TOOTH MOVEMENT AND POSITION MEASURING, MONITORING, AND CONTROL

FIELD

The present disclosure relates to orthodontics. More particularly, the present disclosure relates to an orthodontic system with tooth movement and position measuring, monitoring, and control during orthodontic treatment, the system comprising one or two orthodontic appliances and a programmable control console.

BACKGROUND

Malocclusion is an abnormal alignment of the teeth and is typically characterized by crooked, crowed, or protruding teeth and upper and lower teeth that do not fit together properly. Orthodontic treatment attempts to remedy malocclusion by properly aligning the teeth. One common orthodontic treatment uses an orthodontic appliance to properly align the teeth.

There are many known orthodontic appliances for aligning teeth. The most commonly known orthodontic appliance are braces, which are permanently fixed with respect to the teeth until treatment is completed. Braces typically include brackets that are bonded to individual teeth using a suitable adhesive, and wires that are threaded through or wrapped around a portion of each bracket. The wires apply a force against the teeth via the brackets, which gradually move the teeth into alignment.

In the last couple of decades, removable orthodontic appliances have been developed, which are worn part time or most of the time, day or night. These appliances fit in the intraoral cavity in a manner which allows them to apply a force against the teeth, which gradually move the teeth into alignment, and be easily removed from and refitted in the intraoral cavity by the patient. One such removable orthodontic appliance is described in U.S. Pat. No. 7,819,661, the entire disclosure of which is incorporated herein by reference.

The amount and the duration of the force applied by the orthodontic appliance to the teeth must be controlled over the course of the orthodontic treatment to avoid undesirable effects, such as tooth root resorption and/or pain and discomfort associated with orthodontic appliance.

Accordingly, an orthodontic system is needed with tooth movement and position measuring, monitoring, and control during orthodontic treatment.

SUMMARY

Disclosed herein are an orthodontic appliance for moving and aligning at least one tooth of a set of teeth of at least one of an upper jaw and a lower jaw of a patient, an electronic control console, and an orthodontic system, which in some embodiments, may comprise the orthodontic appliance and the electronic control console. The orthodontic appliance may comprise a force exerting member for applying a force to and moving the at least one tooth, a tooth movement sensor member for obtaining at least one of tooth movement data, tooth position data, and tooth identification data, and a tooth movement monitor for calculating at least one of an amount of tooth movement and tooth position from the at least one of the tooth movement data, the tooth position data, and the tooth identification data obtained with the tooth movement sensor arrangement. The electronic control console may be operatively connected to the force exerting member and in data communication with the tooth movement monitor, for controlling the operation of the force exerting member based on the at least one of the tooth movement data, the tooth position data, and the tooth identification data received from the tooth movement monitor.

In some embodiments, the appliance may further comprise a mouthpiece.

In some embodiments, the force exerting member may be associated with the mouthpiece in a manner that allows physical engagement between the at least one force exerting member and the at least one tooth.

In some embodiments, the tooth movement sensor may be associated with the mouthpiece in a manner that allows physical engagement with the at least one tooth or optical communication with at least one of the at least one tooth and the set of teeth.

In some embodiments, the force exerting member may comprise at least one inflatable element.

In some embodiments, the tooth movement sensor may comprise at least one force sensor, at least one optical image sensor, and any combination thereof.

In some embodiments, the at least one force sensor may comprise at least one contact force sensor, at least one flexible force sensor, and any combination thereof, and the at least one optical sensor may comprise at least one micro video camera, at least one micro still camera, and any combination thereof.

In some embodiments, the at least one force sensor may measure at least one of a force applied thereto by the at least one tooth and a location of the applied force, and the at least one optical image sensor may obtain at least one optical image of at least one of the at least one tooth and the set of teeth.

In some embodiments, the tooth movement monitor may comprise a controller for interrogating the tooth movement sensor member, and in response, receiving the at least one of tooth movement data, tooth position data, and tooth identification data obtained by the tooth movement sensor member, the controller calculating the at least one of the amount of tooth movement and the tooth position from the at least one tooth movement data, tooth position data, and tooth identification data.

In some embodiments, the electronic control console may comprise a fluid pump which causes the force exerting member to apply the force on the at least one tooth.

In some embodiments, the electronic control console may further comprise a controller for selectively controlling the operation of the fluid pump.

In some embodiments, the electronic control console may further comprise at least one fluid sensor and a valve for assisting the controller in selectively controlling the operation of the pump.

In some embodiments, the electronic control console may be programmable.

In some embodiments, the electronic control console and the tooth movement monitor may each comprise a communication interface, the communication interfaces allowing the data communication between the electronic control console and the tooth movement monitor.

In some embodiments, the communication interface of the electronic control console may allow data communication with a communication device operated by the patient, thereby allowing the at least one of the amount of tooth movement and the tooth position, whether in real time or stored, to be communicated by the communication device of the patient to a remotely located communication device of a remotely located dentist or other user.

In some embodiments, the communication interface of the electronic control console may allow receipt of program instructions from the remotely located communication device operated by the dentist or other user, via the communication device operated by the patient, the program instructions programming the controller of the control console.

In some embodiments, the communication interface of the electronic control console may allow receipt of program instructions from a remotely located communication device operated by a dentist or other user, the program instructions programming the controller of the control console.

In some embodiments, the communication interfaces of the electronic control console and the tooth movement monitor may allow a dentist or other user to remotely access the control console and the tooth movement monitor, via a communication device operated by the dentist and a communication device operated by the patient, to initiate a real time measurement of the at least one of the amount of tooth movement and the tooth position, or obtain at least one of the amount of tooth movement and the tooth position stored in the control console.

In some embodiments, the orthodontic appliance may comprise first and second orthodontic appliances, one of the first and second orthodontic appliances for moving and aligning at least one tooth of the set of teeth of the upper jaw of the patient and the other one of the first and second orthodontic appliances for moving and aligning at least one tooth of the set of teeth of the lower jaw of the patient.

Further disclosed herein is a method for moving and aligning at least one tooth of a set of teeth of at least one of an upper jaw and a lower jaw of a patient. The method comprising applying with a force exerting member a force to and moving the at least one tooth, obtaining with a tooth movement sensor member at least one of tooth movement data, tooth position data, and tooth identification data, calculating at least one of an amount of tooth movement and tooth position from the at least one of the tooth movement data, the tooth position data, and the tooth identification data obtained with the tooth movement sensor arrangement, and controlling the operation of the force exerting member with an electronic control console based on the at least one of the tooth movement data, the tooth position data, and the tooth identification data received from the tooth movement monitor.

In some embodiments, the obtaining may comprise interrogating the tooth movement sensor member with a controller, and in response, receiving the at least one of tooth movement data, tooth position data, and tooth identification data obtained by the tooth movement sensor member, the controller calculating the at least one of the amount of tooth movement and the tooth position from the at least one tooth movement data, tooth position data, and tooth identification data.

In some embodiments, the method may further comprise sending, with a communication interface of the electronic control console, the at least one of the amount of tooth movement and the tooth position to a communication device of the patient.

In some embodiments, the method may further comprise sending, with the communication device of the patient, the received at least one of the amount of tooth movement and the tooth position to a remotely located communication device of a remotely located dentist or other user.

In some embodiments, the sending is performed in real time.

In some embodiments, the method may further comprise receiving, with the communication interface, program instructions from the remotely located communication device operated by the dentist or other user, the program instructions programming the controller of the control console.

In some embodiments, the method may further comprise initiating from a remotely located communication device operated by a dentist or other user, via the communication interface, a measurement of the at least one of the amount of tooth movement and the tooth position, or obtain at least one of the amount of tooth movement and the tooth position stored in the controller.

DETAILED DESCRIPTION

Figure 1:
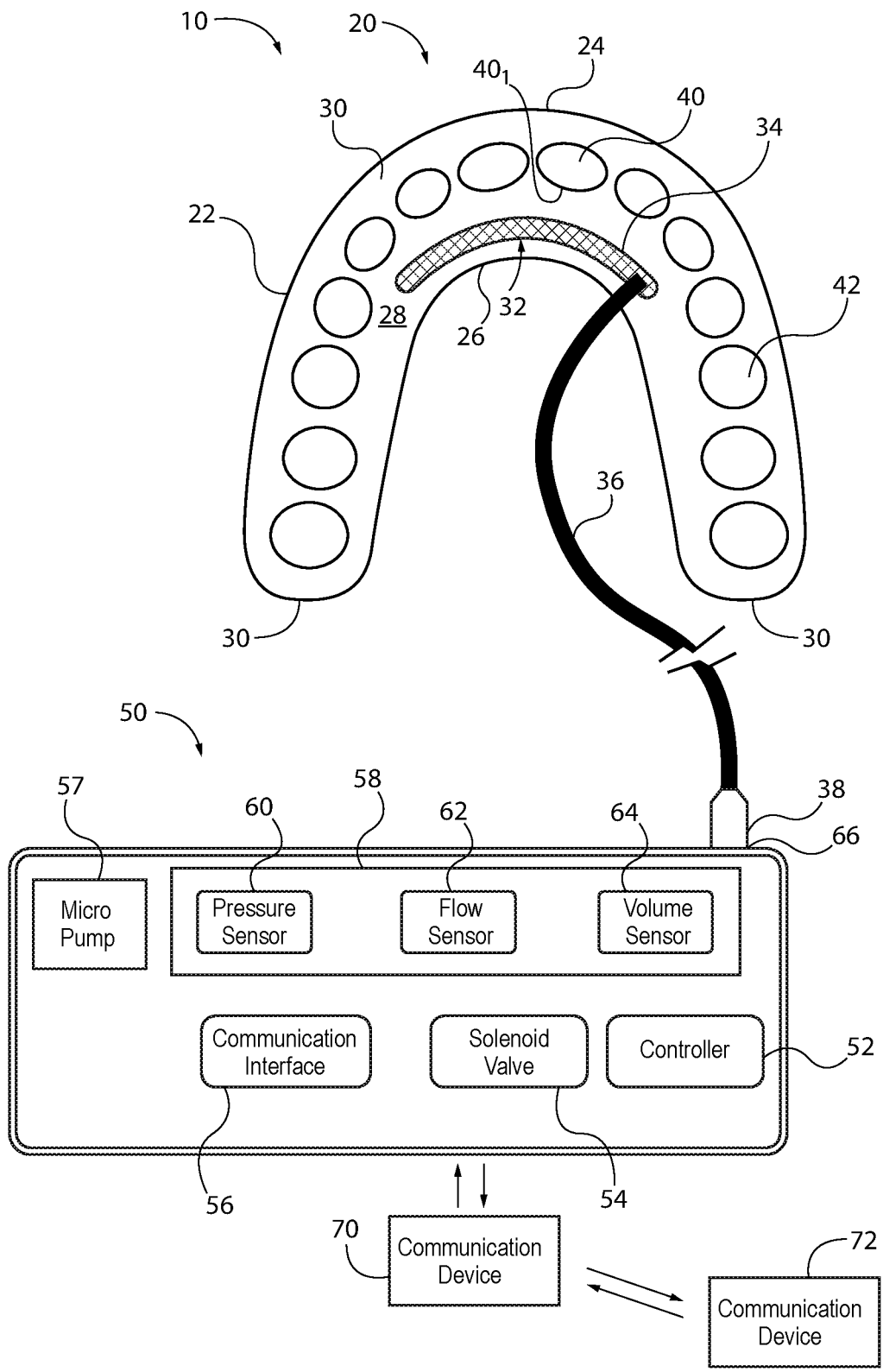
FIG. 1 is a schematic illustration of an orthodontics system according to an embodiment of the present disclosure.

FIG. 1 schematically illustrates an orthodontics system 10 with tooth movement and position measuring, monitoring, and control during orthodontic treatment, according to an embodiment of the disclosure. The system 10 comprises one orthodontic appliance or aligner 20, which receives the teeth 40, 42 of the upper or lower jaw of a patient, and a mobile programmable electronic control console 50. As illustrated in FIG. 2C, other embodiments of the system can comprise a first aligner $20_1$, which receives the teeth 40, 42 of the upper jaw of the patient and a second aligner $20_2$, which receives the teeth 40, 42 of the lower jaw of the patient. The aligner(s) 20, $20_1$, $20_2$ of the system 10 is/are adapted to move and thereby align one tooth 40 or a plurality of teeth 40 (two or more teeth) of the upper and/or lower jaw of the patient.

In the case of one tooth to be aligned 40, the aligner 20 moves and aligns the tooth along a predetermined three-dimensional path. In the case of the plurality of teeth to be aligned 40, the aligner 20 simultaneous moves and aligns the plurality of teeth 40, where each tooth is aligned along a predetermined three-dimensional path. The plurality of teeth to be aligned 40 may be adjacent to one another, spaced one from another, arranged in groups, or comprising all the teeth in the same arch of the intraoral cavity. Therefore, in various embodiments, one or more of the teeth may be aligned by the aligner 20, where one or more of these teeth 40 may be moved lingually and one or more of these teeth 40 may be moved in the buccal/labial direction.

The aligner 20 may comprise a generally U-shaped mouthpiece 22, a force exerting member or arrangement 32, which applies a force to and moves the one or more teeth to be aligned 40, a tooth movement sensor member or arrangement 80, 84, $86_1$, $86_2$, 88 (see FIGS. 2A-2D), which obtains tooth movement and/or position data, and a tooth movement monitor 82, which calculates tooth movement and/or tooth position using the tooth movement and/or position data obtained by the tooth movement sensor arrangement 80, 84, $86_1$, $86_2$, 88.

The mouthpiece 22 may comprise a channel 30 formed by a curved labial/buccal (facial) wall 24, a curved lingual wall 26, an incisal/occlusal (base) wall 28 connecting the facial wall 24 and lingual wall 26, and posterior walls 30 connecting posterior ends of the facial wall 24 and lingual wall 26. The channel 30 can be adapted to receive teeth 40, 42 of a patient's upper or lower jaw. The facial wall 24 and the lingual wall 26 both extend along the facial and lingual surfaces of the teeth 40, 42 of the dental arch of the jaw, and the base wall 28 extends along the incising edges of the teeth 40, 42, when the mouthpiece 22 is inserted into the mouth. In some embodiments, where the facial wall 24 and lingual wall 26 are connected to the base wall 28, the posterior walls 30 can be omitted so that the ends of the channel 30 are open. Such embodiments may be useful where it is desirable to reduce the length the facial wall 24 and lingual wall 26 so that they do not extend past certain teeth 42 not being aligned, including, but not limited to the second and/or third molars or other teeth 42 of the dental arch of the jaw not being aligned. The mouthpiece 22 can be made from a transparent, semi-transparent or opaque dental-compatible material, which may be rigid or at least sufficiently rigid to ensure that the mouthpiece 22 does not deform under the tooth aligning force(s). Suitable materials for the mouthpiece 22 include, without limitation, thermoplastic polycarbonate, acrylic resin, and like materials.

The force exerting arrangement 32 can comprise one or more inflatable elements 34 (also referred to hereinafter as inflatable element 34 or inflatable element(s) 34 disposed within the mouthpiece 22. The inflatable element 34 applies a force to each tooth to be aligned 40 in a manner which moves each tooth 40 along a three-dimensional path that has been predetermined to be suitable for that particular tooth 40. In the embodiment illustrated in FIG. 1, the inflatable element 34 can be located between each tooth to be aligned 40 and the lingual wall 26 of the mouthpiece 22, to exert a force on the lingual surface $40_1$ of the tooth 40. In other embodiments (not illustrated), the inflatable element can be located between each tooth to be aligned and the facial wall of the mouthpiece, to exert a force on the facial surface of the tooth. In further embodiments (not illustrated), at least a first inflatable element can be located between one or more teeth to be aligned and the facial wall of the mouthpiece, to exert a force on the facial surface(s) of these teeth, and at least a second inflatable element can be located between one or more of other teeth to be aligned and the lingual wall, to exert force on the lingual surface(s) of these teeth. The location of the inflatable element(s) within the mouthpiece depends upon each tooth's predetermined three-dimensional aligning path. The inflatable element(s) 34 can be attached to or partially embedded in, the inner surface of the facial wall 24 and/or the lingual wall 26, and/or base wall 28 of the mouthpiece 22.

Each inflatable element 34 can comprise, without limitation, an inflatable sleeve or balloon, which can be inflated and deflated via a fluid conduit or tube 36 that extends from the inflatable element(s) 34 to allow fluid connection thereof to the programmable electronic control console 50, which selectively inflates and deflates the inflatable element(s) 34 using fluid pressure. Typically, the inflatable element 34, when deflated, does not exert a force against the tooth or teeth 40 and may or may not make contact therewith. When inflated, the inflatable element 34 expands and contacts the one or more teeth to be aligned 40, thereby applying a force which urges the one or more teeth 40 in the desired direction (the predetermined three-dimensional path).

The programmable electronic control console 50 of the system 10 can comprise a fluid micro pump 57, a fluid sensor arrangement 58, a solenoid valve 54, a controller 52 for controlling the operation of the micro pump 57 and solenoid valve 54 and a communication interface 56. The micro pump 57 of the console 50 can be connected to the inflatable element(s) 34 of the aligner 20 via the fluid tube 36, which extends from the aligner 20 and fluidically communicates with the inflatable element(s) 34. The micro pump 57 pumps a fluid, via the fluid tube 36, which inflates and expands the inflatable element(s) 34. A connector 38 can be provided at the free end of the fluid tube 36 so it can be removably connected to an outlet 66 of the micro pump 57 located externally on the control console 50. The solenoid valve 54 of the control console 50 can be adapted to allow the patient, doctor and/or other end user to adjust the fluid pressure of the micro pump 57 and release the fluid pressure to deflate the one or more inflatable elements 34, prior to disconnecting the fluid tube 36 from the control console 50.

The micro pump 57 can comprise a piezoelectric micro pump, an electrostatic micro pump, a pneumatic micro pump, or any other suitable pump that is capable of inflating the inflatable element(s) 34 and fitting inside of the mobile control console 50. The inflatable elements 34 can be inflated using any suitable fluid including, without limitation, air, another suitable gas, water, or any other suitable fluid, and the micro pump 57 of the console 50 can be adapted to pump any of these fluids.

The controller 52 of the control console 50 selectively controls the operation of the micro pump 57 so that the force exerted by the inflatable element(s) 34 on the one or more teeth 40, when inflated by the micro pump 57, may be constant, varied, or a combination thereof. The controller 52 is adapted to be programed locally or remotely by a dentist, dental technician, and/or patient. The inflatable element(s) 34 can be made to exert a constant force and/or pulsating force of a desired magnitude on one or more teeth to be aligned 40 by programming the controller 52 to energize the micro pump 57 so that it inflates to a pressure which expands the inflatable element(s) 34 and causes it to exert and maintain the desired force, as the one or more teeth to be aligned 40 move along their predetermined three-dimensional path.

The controller 52 of the console 50 can also be programmed to selectively operate the micro pump 57 and the solenoid valve 54, such that the micro pump 57 inflates and expands the inflatable element(s) 34 and the solenoid valve 54 deflates and contracts the inflatable element(s) 34 in manner that causes it to exert a varied force on one or more teeth to be aligned 40, for example, in the form of periodic pulses, which provide a pulsating force to the one or more teeth to be aligned 40. When so programmed, the controller 52 cyclically (at a desired frequency selected by the dentist or dental technician) energizes and de-energizes the micro pump 57 and solenoid valve 54 at the appropriate times, so that the micro pump 57 inflates and expands the inflatable element(s) 34 causes it to exert a desired force for a certain time period on the one or more teeth to be aligned 40 and then de-energizes the micro pump 57 and opens the solenoid valve 54 for a certain time period, to release the fluid pressure and deflate and contracts the inflatable element(s) 34.

The controller 52 of the console 50 can be programmed by the dentist or dental technician to stop the operation of the micro pump 57 and open the solenoid valve 54 to terminate the force exerted by the inflatable element(s) 34 on the one or more teeth to be aligned 40, when they arrive at their final position(s). The controller 52 of the control console 50 can store tooth movement and/or position data obtained by tooth movement monitor 82 of each the aligner 20 of the system 10. The control console controller 52 may comprise but is not limited to a microcontroller, microprocessor with external memories or a field programmable gate array (FPGA).

Referring still to FIG. 1, the fluid sensor arrangement 58 of the control console 50 provides the controller 52 with micro pump performance data, which can be used by the controller 52 to selectively control the operation of the micro pump 57. The fluid sensor arrangement 58 can comprise a fluid pressure sensor 60, a fluid flow sensor 62, and fluid volume sensor 64. The fluid pressure sensor 60 detects the fluid pressure of the micro pump 57, the fluid flow sensor 62 measures the fluid flow rate of the micro pump 57, and the fluid volume sensor 64 measures the fluid volume of the micro pump 57. The fluid pressure, flow, and volume measurements can be used by the controller 52 of the console 50 to control the energizing and the speed of the pump speed, so that the micro pump 57 maintains desired inflation pressure and corresponding tooth moving forces.

The console communication interface 56 of the control console 50 can be adapted to receive tooth movement and/or position data obtained with tooth movement monitor 82, as will be explained further on.

Figure 2A:
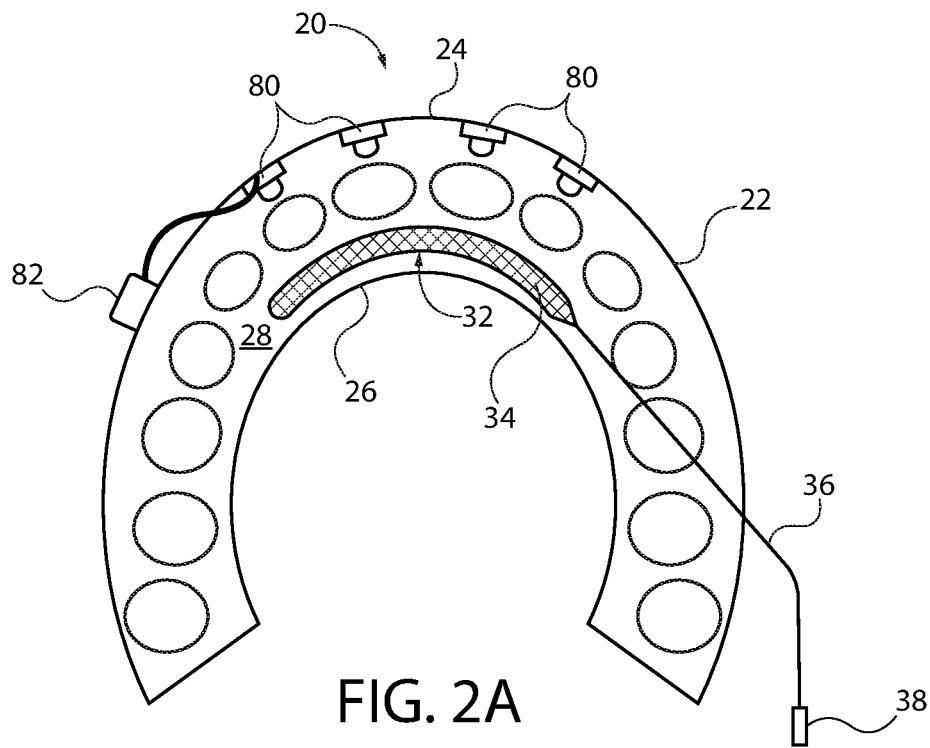
FIG. 2A is a schematic illustration of an embodiment of a tooth movement sensor arrangement of an aligner of the system.

FIG. 2A schematically illustrates an embodiment where the tooth movement sensor arrangement of the aligner 20 comprises one or more contact force sensors 80 arranged within the mouthpiece 22 of the aligner, so that each force sensor 80 is adjacent to a tooth to be aligned 40 with the aligner 20. When the force sensor 80 is engaged by a tooth 40 moved by an inflatable element 34, the sensor 80 measures the amount of force exerted by the moving tooth 40 and generates a signal (wired, wireless, or optical) representing the measured amount of force, which can be used by the tooth movement monitor 82 to calculate the movement of the tooth 40 in real time or the amount of movement since a previous force measurement/tooth movement calculation. Each of the one or more force sensors 80 may comprise a pressure sensor, such as but not limited to a piezoresistive force sensor, a strain gauge, a load cell, or any other suitable pressure sensor. The one or more contact force sensors 80 can be attached to or partially embedded in the interior surface of the facial wall 24 and/or the lingual wall 26 and/or the base wall 28 of the mouthpiece 22, such that each sensor 80 contacts the side of the tooth 40, which is opposite the inflatable element(s) 34.

Figure 2B:
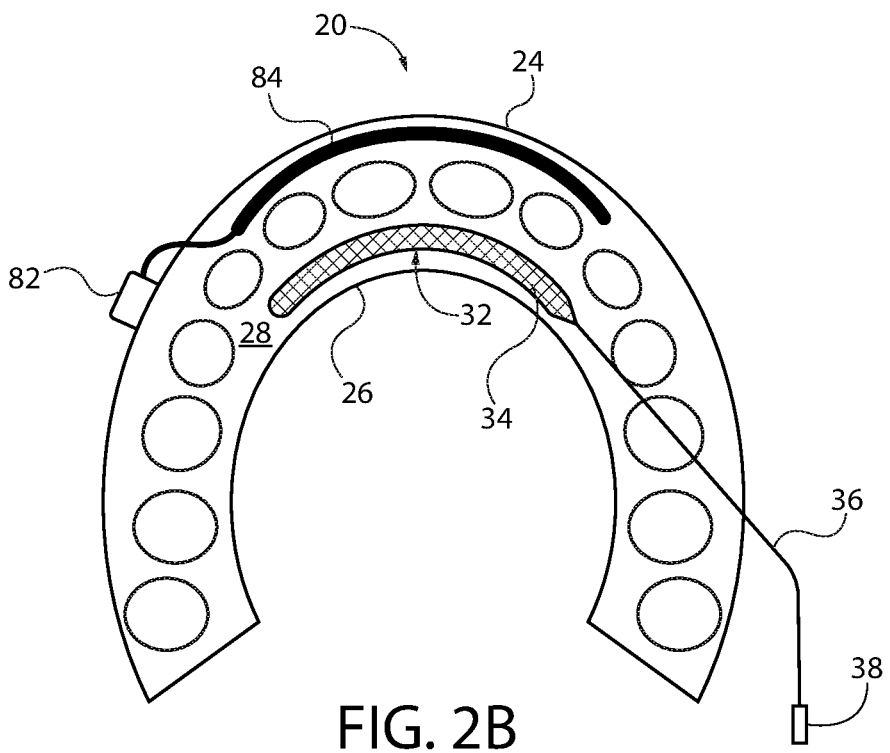
FIG. 2B is a schematic illustration of another embodiment of the tooth movement sensor arrangement of the aligner of the system.
Figure 2C:
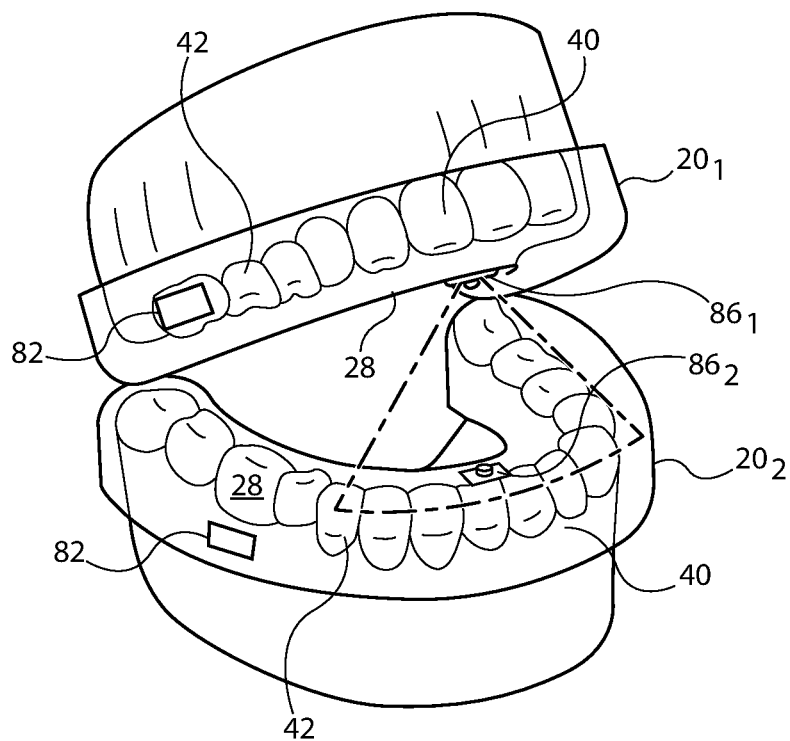
FIG. 2C is a schematic illustration of further embodiment of the tooth movement sensor arrangement of the aligner of the system.

FIG. 2B schematically illustrates an embodiment where the tooth movement sensor arrangement of the aligner 20 comprises one or more flexible force sensors 84 arranged within the mouthpiece 22 of the aligner 20 adjacent to one or more teeth to be aligned 40 with the aligner 20. When the flexible force sensor(s) 84 is engaged by one or more of the teeth 40 moved by inflatable element(s) 34, it measures an input representing the measured amount of force and the location applied by the tooth on the flexible force sensor(s) 84, which can be used by the tooth movement monitor 82 to calculate the movement of the tooth 40 in real time and/or the area where force has been applied. Each of the one or more flexible force sensors 84 may comprise a FlexiForce® force sensor marketed and sold by Tekscan® or a Force Sensing Resistor® marketed and sold by Interlink Electronics®. The one or more flexible force sensors 84 can be attached to or embedded in the interior surface of the facial wall 24 and/or the lingual wall 26 and/or the base wall 28 of the mouthpiece 22, such that each sensor 84 contacts the side of the tooth 40, which is opposite the inflatable element(s) 34.

FIG. 2C schematically illustrates an embodiment comprising a first aligner $20_1$ (transparent in this embodiment), which aligns one or more teeth 40 of the upper jaw and a second aligner $20_2$ (transparent in this embodiment), which aligns one or more teeth 40 of the lower jaw. The tooth movement sensor arrangement of the first aligner $20_1$ can comprise at least a first optical image sensor $86_1$, which can be attached to or partially embedded in an exterior surface of the base wall 28 of the first aligner's mouthpiece 22 (or fully embedded in the base wall 28). The first optical image sensor(s) $86_1$ can capture an optical image of the position of at least the one or more teeth to be aligned 40 of the opposite lower jaw, through the transparent second aligner $20_2$. The tooth movement sensor arrangement of the second aligner $20_2$ can comprise at least a second optical image sensor $86_2$, which can be attached to or partially embedded in an exterior surface of the base wall 28 of the second aligner's mouthpiece 22 (or fully embedded in the base wall 28). The second optical image sensor(s) $86_2$ can capture an optical image of the position of at least the one or more teeth to be aligned 40 of the opposite upper jaw, through the transparent first aligner $20_1$. The optical image sensors $86_1$, $86_2$ generate signals (wired, wireless, or optical) representing the captured optical images (video or still), which can be used by the tooth movement monitors $82_1$, $82_2$ to calculate the movement and position of each tooth 40 in real time or the amount of tooth movement since a previously calculated tooth position. Each of the optical image sensors $86_1$, $86_2$ may comprise, without limitation, a micro video camera, a micro still camera or any other suitable image sensor, which can be unobtrusively integrated within the mouthpiece 22 of the aligner $20_1$, $20_2$ and can convert optical images into signals (wired, wireless, or optical).

Figure 2D:
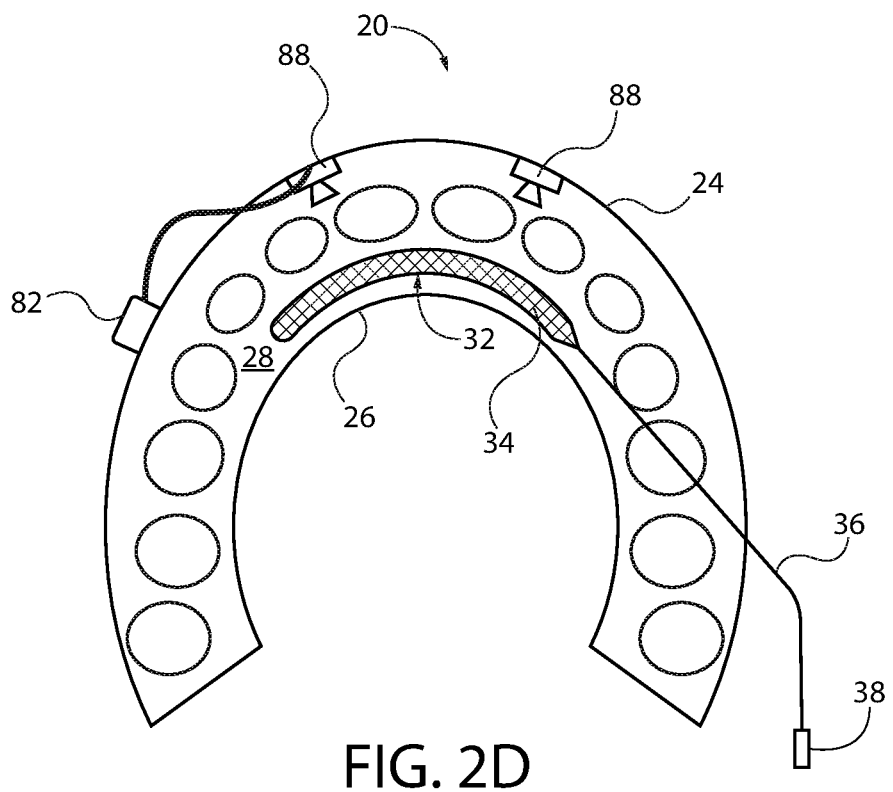
FIG. 2D is a schematic illustration of still another embodiment of the tooth movement sensor arrangement of the aligner of the system.

FIG. 2D schematically illustrates an embodiment where the tooth movement sensor arrangement of the aligner 20 comprises one or more optical image sensors 88 arranged within the mouthpiece 22, which each captures optical images of the position of at least the one or more teeth to be aligned 40 with the aligner 20. Each optical image sensor 88 generates a signal (wired, wireless, or optical) representing the captured optical image (video or still), which can be used to calculate the movement and position of each tooth in the image in real time or the amount of movement since a previously calculated tooth position. Each of the image sensors 88 may comprise, without limitation, a micro video camera, a micro still camera, or any other suitable image sensor, which can be unobtrusively integrated within the mouthpiece 22 of the aligner 20 and can convert optical images into signals (wired, wireless, or optical). The one or more optical image sensors can be attached to or embedded in the inner surface of the facial wall 24 and/or the lingual wall 26 and/or the base wall 28 of the mouthpiece 22, such that each sensor can obtain an optical image of at least the one or more teeth to be aligned 40 with the aligner 20.

In other embodiments, the tooth movement sensor arrangement of the aligner 20 can comprise any combination of the earlier described contact force, flexible force, and optical image sensors 80, 84, 86₁, 86₂, 88.

The tooth movement sensor arrangement 80, 84, 86₁, 86₂, 88, such as described above and illustrated in FIGS. 2A-2D, can be communicatively connected (e.g., wired, wireless, or optically) to or with a tooth movement monitor 82. The wireless connection can be implemented using any suitable radio frequency (RF) method including but not limited to Bluetooth®, wireless fidelity (Wi-Fi), and/or radio frequency identification (RFID). Optical connections can be implemented using any suitable optical communication method such as, but not limited to infrared (IR).

Figure 3:
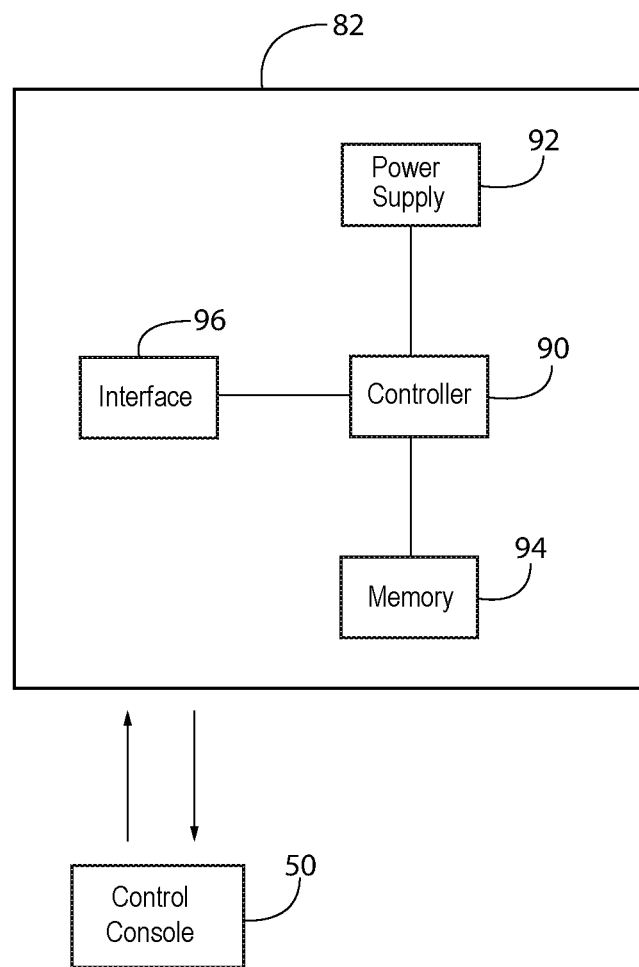
FIG. 3 is a block diagram of an embodiment of a tooth movement monitor of the aligner of the system.

Referring to FIG. 3, the tooth movement monitor 82 can include a controller 90, a power supply 92 connected to the controller 90, and a memory 94 connected to the controller 90. The controller 90 receives input from the tooth movement sensor arrangement 80, 84, 86₁, 86₂, 88. The tooth movement monitor 82 can further include a communication interface 96 connected to the controller 90, which allows the tooth movement monitor 82 to communicate with the programmable electronic control console 50.

The tooth movement monitor 82, via the controller 90, can be adapted to interrogate the tooth movement sensor arrangement, and in response, receive tooth movement and/or position data in the form of a force measurement signal and/or an optical tooth image signal respectively representing a force measurement and/or an optical tooth image obtained by the tooth movement sensor arrangement 80, 84, 86₁, 86₂, 88 (FIGS. 2A-2D) in response to interrogation by the controller 90. The controller 90 of the tooth movement monitor 82 can then use this data to calculate in real time the amount each tooth to be aligned 40 has moved and its current position, and/or the amount each tooth to be aligned 40 has moved relative to a previously calculated tooth position stored in the memory by the monitor 82. In some embodiments, 3D files representing the pretreatment position of the teeth and the Setup (final position of the teeth) are obtained for use in manufacturing the mouthpiece 22 for a patient. Any sub-step between the pretreatment position and the Setup can then be derived, as described above with the tooth movement monitor 82. The calculation performed by the controller 90 of the monitor 82 can be based on the amount of force that is measured by each force sensor and/or the volume change of the inflatable element(s) and the differential between these forces.

The controller 90 of the tooth movement monitor 82 may comprise without limitation a microcontroller, microprocessor, application specific integrated circuit (ASIC), or field programmable gate array (FPGA).

The communication interface 96 of the tooth movement monitor 82 (FIG. 3) and the communication interface 56 of the programmable electronic control console 50 (FIG. 1), can be adapted to communicate with one another via a wired, wireless, or optical connection. This allows the tooth movement monitor 82 to send tooth movement and position data to the control console 50. In addition, the two-way communication between the tooth movement monitor 82 and the control console 50 allows a dentist or other dental technician to use the control console 50 to obtain real time tooth movement and/or position measurement via the tooth movement monitor 82. The wireless communication can be implemented using any suitable radio frequency (RF) method including but not limited to Bluetooth®, wireless fidelity (Wi-Fi), and/or radio frequency identification (RFID). Optical communication can be implemented using any suitable optical communication method such as, but not limited to infrared (IR).

The control console communication interface 56, in some embodiments, may be further adapted to communicate with a communication device 70 used by a patient, which may include, without limitation, a hand-held mobile device such as a smartphone, a tablet computer, and/or a personal computer, via the wired, RF and/or optical methods described earlier. The communication device 70 can be communicatively connected to a cellular network, such as a mobile phone network, and/or a computer network, such as the Internet. So adapted, the console communication interface 56 allows the control console 50 to send real time or stored tooth movement and/or position data (stored in the controller 52 of the control console 50 and/or the controller 90 of the tooth movement monitor 82), via the patient's communication device 70, to a communication device 72 used by a remotely located dentist or dental technician. The communication device 72 used by the dentist or dental technician may include, without limitation, a hand-held mobile device, such as a smartphone, a tablet computer, and/or a personal computer. The dentist or dental technician, in turn, may then use the communication device 72 to send a new program to the controller 52 of the control console 50, via the patient's communication device, from the remote location, in response to the tooth movement data received from the control console 50. In addition, the dentist or dental technician can remotely access the control console 50, via communication devices 70 and 72, and initiate a real time measurement of tooth movement and position via the tooth position monitor 82 and control console, or obtain tooth movement and position data stored in the control console 50.

Although the orthodontic system, its individual components, and their corresponding methods of operation and use have been described in terms of illustrative embodiments, they are not limited thereto. Rather, the appended claims should be construed broadly to comprise other variants and embodiments of the orthodontic system, its individual components, and their corresponding methods of operation and use, which may be made by those skilled in the art without departing from the scope and range of equivalents of the same.

What is claimed is:

1. An orthodontic system comprising:
 a mouthpiece for applying to a set of teeth of one of an upper jaw and a lower jaw of a patient, the mouthpiece comprising:
 a force exerting member for moving at least one tooth of the set of teeth of the one of the upper jaw and the lower jaw of the patient;
 a tooth movement sensor member for obtaining tooth data, the tooth movement sensor being one of:
 a force sensor attached to or partially embedded in the interior surface of a facial, lingual, or base wall, or a combination thereof of the mouthpiece, such that the force sensor is adapted to contact a side of the at least one tooth, which is opposite a side of the tooth adapted to be in contact with the force exerting member, and
 an optical sensor; and
 a tooth movement monitor for calculating an amount of tooth movement and/or a tooth position from the tooth data obtained with the tooth movement sensor member; and
 an electronic control console operatively connected to the force exerting member and in data communication with the tooth movement monitor; the electronic control console controlling the operation of the force exerting member based on the tooth data received from the tooth movement monitor.

2. The orthodontic system of claim 1; wherein the force exerting member is adapted to physically engage the at least one tooth when the system is used by the patient.

3. The orthodontic system of claim 1; wherein the tooth movement sensor member is adapted to be physically engaged by the at least one tooth when the system is used by the patient or wherein the tooth movement sensor member optically communicates with at least one tooth when the system is used by the patient.

4. The orthodontic system of claim 1; wherein the force exerting member comprises an inflatable element.

5. The orthodontic system of claim 4; wherein the electronic control console comprises a fluid pump for inflating the inflatable element.

6. The orthodontic system of claim 5; wherein the electronic control console further comprises a programable controller for selectively controlling the operation of the fluid pump.

7. The orthodontic system of claim 1, wherein the tooth movement sensor member comprises at least one force sensor selected from the group of:
a contact force sensor and a flexible force sensor, at least one optical image sensor selected from the group of a micro video camera, a micro still camera, and an image sensor, or any combination thereof.

8. The orthodontic system of claim 1, wherein the tooth movement monitor comprises a controller for calculating the amount of tooth movement and/or the tooth position from the tooth data.

9. The orthodontic system of claim 1, wherein the electronic control console and the tooth movement monitor each comprises a communication interface, the communication interfaces allowing the data communication between the electronic control console and the tooth movement monitor.

10. The orthodontic system of claim 9, wherein the communication interface of the electronic control console allows data communication with a communication device operated by the patient, thereby allowing the amount of tooth movement and/or the tooth position to be communicated by the communication device of the patient to a remotely located communication device of a remotely located dentist or other user.

11. The orthodontic system of claim 10, wherein the electronic control console comprises a programmable controller and wherein the communication interface of the electronic control console allows receipt of program instructions from the remotely located communication device operated by the dentist or other user, via the communication device operated by the patient, the program instructions programming the programmable controller of the electronic control console.

12. The orthodontic system of claim 9, wherein the electronic control console comprises a programmable controller and wherein the communication interface of the electronic control console allows receipt of program instructions from a remotely located communication device operated by a dentist or other user, the program instructions programming the controller of the electronic control console.

13. The orthodontic system of claim 9, wherein the communication interfaces of the electronic control console and the tooth movement monitor allow a dentist or other user to remotely access the control console and the tooth movement monitor, via a communication device operated by the dentist and a communication device operated by the patient, to initiate a real time measurement of the amount of tooth movement and/or the tooth position, or obtain the amount of tooth movement and/or the tooth position stored in the electronic control console.

14. The orthodontic system of claim 1, further comprising a second mouthpiece for applying to a set of teeth of the other one of the upper jaw and the lower jaw of the patient, the second mouthpiece comprising,
a second force exerting member for moving at least one tooth of the set of teeth of the other one of the upper jaw and the lower jaw of the patient,
a second tooth movement sensor member for obtaining tooth data, and
a second tooth movement monitor for calculating an amount of tooth movement and/or a tooth position from the tooth data obtained with the second tooth movement sensor member, and
wherein the electronic control console is operatively connected to the second force exerting member of the second mouthpiece and in data communication with the tooth movement monitor of the second mouthpiece, the electronic control console controlling the operation of the second force exerting member based on the tooth movement data, the tooth position data, and/or the tooth identification data received from the second tooth movement monitor.

15. A mouthpiece for applying to a set of teeth of one of an upper jaw and a lower jaw of a patient, the mouthpiece comprising:
a force exerting member for moving at least one tooth of the set of teeth of the one of the upper jaw and the lower jaw of the patient,
a tooth movement sensor member for obtaining tooth data, the tooth movement sensor being one of:
a force sensor attached to or partially embedded in the interior surface of a facial, lingual, or base wall, or a combination thereof of the mouthpiece, such that the force sensor is adapted to contact a side of the at least one tooth, which is opposite a side of the tooth adapted to be in contact with the force exerting member, and
an optical sensor, and
a tooth movement monitor for calculating an amount of tooth movement and/or a tooth position from the tooth data obtained with the tooth movement sensor member.

16. The mouthpiece of claim 15, wherein the force exerting member is adapted to physically engage the at least one tooth when the system is used by the patient.

17. The mouthpiece of claim 15, wherein the tooth movement sensor member is adapted to be physically engaged by the at least one tooth when the system is used by the patient or wherein the tooth movement sensor member optically communicates with at least one tooth when the system is used by the patient.

18. The mouthpiece of claim 15, wherein the force exerting member comprises an inflatable element.

19. The mouthpiece of claim 15, wherein the tooth movement sensor member comprises at least one force sensor selected from the group of:
a contact force sensor and a flexible force sensor, at least one optical image sensor selected from the group of a micro video camera, a micro still camera, and an image sensor, or any combination thereof.

20. The mouthpiece of claim 15, wherein the tooth movement monitor comprises a controller for calculating the amount of tooth movement and/or the tooth position from the tooth data.

21. An orthodontic system comprising:
- a mouthpiece for applying to a set of teeth of one of an upper jaw and a lower jaw of a patient, the mouthpiece comprising:
- a force exerting member for moving at least one tooth of the set of teeth of the one of the upper jaw and the lower jaw of the patient, and
- a tooth movement sensor member for obtaining tooth data, the tooth movement sensor being one of:
  - a force sensor attached to or partially embedded in the interior surface of a facial, lingual, or base wall, or a combination thereof of the mouthpiece, such that the force sensor is adapted to contact a side of the at least one tooth, which is opposite a side of the tooth adapted to be in contact with the force exerting member, and
  - an optical sensor, and
- an electronic control console operatively connected to the force exerting member, the electronic control console comprising:
- a programable controller for selectively controlling the operation of the force exerting member, and
- a communication interface for allowing receipt of program instructions from a remotely located communication device operated by a dentist or other user, the program instructions programming the controller.

* * * * *